US00PP10031P

Jnited States Patent [19]

lielander

[11] Patent Number: Plant 10,031

[45] Date of Patent: Sep. 16, 1997

4] KALANCHOE PLANT NAMED 'KERINCI'

5] Inventor: Ike Vlielander, De Lier, Netherlands

3] Assignee: Fides Beheer B.V., De Lier, Netherlands

1] Appl. No.: 618,044

2] Filed: Mar. 18, 1996

1] Int. Cl.[6] ..... A01H 5/00

2] U.S. Cl. ..... Plt./87.15

8] Field of Search ..... Plt./87.15

[56] References Cited

U.S. PATENT DOCUMENTS

P.P. 5,894 3/1987 Finger ..... Plt./87.15

*Primary Examiner*—Howard J. Locker

*Attorney, Agent, or Firm*—C. A. Whealy

[57] ABSTRACT

A distinct cultivar of Kalanchoe plant named Kerinci, characterized by its dark pink flower color; moderately vigorous plant growth habit; rapid growth rate; freely branching habit; proportional leaf size to plant size; uniform plant habit and inflorescence display; early flowering; floriferousness; and good postproduction longevity.

1 Drawing Sheet

1

The present invention relates to a new and distinct cultivar Kalanchoe plant, botanically known as *Kalanchoe bloss-ldiana*, and hereinafter referred to by the cultivar name erinci.

The new cultivar is a product of a planned breeding ogram conducted by the inventor in De Lier, The Neth-lands. The objective of the breeding program was to create w Kalanchoe cultivars having a uniform plant habit, good wer and foliage colors, and flowers and foliage with good bstance.

The new cultivar originated from a cross made by the ventor of the Kalanchoe cultivar Santorini (not patented) the male or pollen parent with the Kalanchoe cultivar ebessy (disclosed in U.S. Plant Pat. No. 7,767) as the nale or seed parent.

The cultivar Kerinci was discovered and selected by the ventor as a flowering plant within the progeny of the stated oss in a controlled environment in De Lier, The Nether-nds. Asexual reproduction of the new cultivar by terminal ttings taken at De Lier, The Netherlands, has shown that e unique features of this new Kalanchoe are stabilized and oduced true to type in successive generations.

The cultivar Kerinci has not been observed under all ssible environmental conditions. The phenotype may vary mewhat with variations in environment such as tempera-re, daylength and light intensity, without, however, any riance in genotype. The following observations, measure-ents and comparisons describe plants grown in De Lier, e Netherlands, under commercial practice in a glass-vered greenhouse with day temperatures ranging from 19 21 C. and night temperatures ranging from 18 to 19 C.

The following traits have been repeatedly observed and e determined to be the unique characteristics of Kerinci. ese characteristics in combination distinguish Kerinci as new and distinct cultivar:

1. Dark pink flower color.
2. Moderately vigorous plant growth habit and rapid owth rate.
3. Freely branching habit with shoots forming at every de. Plants do not require pinching.
4. Proportional leaf size to plant size.
5. Suitable for various container sizes from 10 to 12 cm.
6. Uniform plant habit and inflorescence display.
7. Early flowering.
8. Very floriferous with numerous flowers per plant.
9. Good postproduction longevity.

The new Kalanchoe differs from the parent cultivar San-ini in the following characteristics:

2

1. Plants of the cultivar Kerinci are more compact and more uniform in plant habit than plants of the cultivar Santorini.
2. The petal color of plants of the cultivar Kerinci is dark pink whereas the petal color of plants of the cultivar Santorini is orange.

Plants of the cultivar Kerinci are most similar in petal color to the female parent, the cultivar Kiebessy. The cultivar Kerinci differs from the cultivar Kiebessy in the following characteristics:

1. Plants of the cultivar Kerinci are more compact and more uniform in plant habit and inflorescence display than plants of the cultivar Kiebessy.
2. Plants of the cultivar Kerinci have shorter lateral branches and internodes than plants of the cultivar Kiebessy.
3. Plants of the cultivar Kerinci have smaller but more leaves per lateral branch than plants of the cultivar Kiebessy.
4. Plants of the cultivar Kerinci flower several days earlier than plants of the cultivar Kiebessy.
5. Petal color of plants of the cultivar Kerinci fade less with age compared to the petal color of plants of the cultivar Kiebessy.

A detailed comparison of the cultivars Kerinci and Kiebessy appears in Chart A at the end of the specification.

The accompanying colored photograph illustrates the overall appearance of the new cultivar, showing the colors as true as it is reasonably possible to obtain in colored reproductions of this type.

The photograph comprises a top perspective view of a typical potted plant of Kerinci taken under natural light conditions at approximately noon in De Lier, The Netherlands.

In the following description, color references are made to The Royal Horticultural Society Colour Chart except where general terms of ordinary dictionary significance are used. Measurements and numerical values represent averages for twelve typical plants in 10.5-cm containers and treated with daminozide growth retardant at a rate of 4 grams per liter.

Botanical classification: *Kalanchoe blossfeldiana* cultivar Kerinci.

Parentage:

*Male or pollen parent.*—*Kalanchoe blossfeldiana* cultivar Santorini (not patented).

*Female or seed parent.*—*Kalanchoe blossfeldiana* cultivar Kiebessy (U.S. Plant Pat. No. 7,767).

Propagation:

*Type cutting.*—Terminal cuttings.

*Time to initiate roots.*—12 days at 21 C. soil temperature.

*Rooting habit.*—Numerous, fine, fibrous, and well-branched.

Plant description:

*Form.*—Upright and uniform. Plant shape is an inverted triangle with a rounded apex. Actual plant shape will depend on whether or not plants are pinched (vegetative terminals removed).

*Branching habit.*—Freely branching, generally shoots formed at every node. Typically 6 to 7 lateral branches will develop with 10 to 15 leaves each.

*Plant height at flowering.*—From soil level to top of plant, 22 cm, appropriate for 10 to 12-cm containers.

*Vigor.*—Moderately vigorous, but rapid growth rate.

*Crop time.*—Three to four weeks of long day/short night conditions followed by 7.5 to 11 weeks of short day/long night conditions are required to produce flowering plants. Depending on temperature and light levels, a total of 10.5 to 15 weeks is required.

*Foliage description.*—Leaves simple, opposite, generally symmetrical. Size: Length: 11.5 cm. Width: 8 cm. Shape: Elliptic. Apex: Acute to obtuse. Base: Acute. Margin: Crenate. Texture: Leathery, glabrous, coriaceous and succulent. Petiole length: 1.6 cm. Color: Young foliage upper side: 137A. Young foliage under side: 137B. Mature foliage upper side: 137A. Mature foliage under side: 137B. Petiole: 137A. Stem color: 137A. Venation upper side: 137A/137B. Venation under side: 137B.

Flower description:

*Flower type and habit.*—Single flowers arranged in panicles, compound dichasial cymes on strong peduncles. Freely flowering and very floriferous with new buds continuing to develop. Uniform inflorescence display.

*Natural flowering season.*—Autumn/winter in Northern Hemisphere. Flower initiation and development can be induced under short day/long night conditions. Opening of new buds will continue for at least seven weeks. Individual flowers last about 17 days after opening. Flowers persistent.

*Inflorescences borne.*—Above foliage, arising from leaf axils. Inflorescence of each shoot is formed by dichotomous branching.

*Time to flower.*—Under warm growing temperatures, 25 C., plants of the cultivar Kerinci will start flowering after 7.5 weeks of exposure to controlled photoperiods (short day/long night conditions). Under cooler growing temperatures, 20 C., plants of the cultivar Kerinci will flower after 11 weeks of exposure to controlled photoperiods. First flower open is the terminal flower at the main axis and is followed by the opening of the terminal flowers of the side branches of the inflorescence.

*Flower diameter.*—1.7 cm.

*Flower depth (height).*—1.4 cm.

*Quantity.*—At least 200 flowers per plant.

*Flower buds.*—Size: Length: 9 mm. Width: 2.5 mm. Shape: Oblong becoming tubular/ovoid with development. Rate of opening: Relatively rapid. Color: Initially 138C becoming 49D just before opening.

*Petals.*—Quantity: 4 fused at base to form bell-shaped corolla. Size: Length: 8 mm. Width: 5 mm. Shape: Ovate. Apex: Acute. Margin: Entire. Texture: Glabrous, smooth and satiny. Aspect: Flat to somewhat upright. Color: When opening: 52A. Mature, upper side: 52B. Mature, under side: 49D/50D. Fading to: 55A. After senescence: 54C/54D.

*Sepals.*—Quantity: 4. Shape: Oblong, pointed. Apex: Acute. Margin: Entire. Texture: Glabrous. Aspect: Upright, rigid. Color: Upper side: 138D, glossy. Under side: 138D, glossy.

*Calyx.*—Size: 9 mm. Shape: Funnel. Texture: Glabrous. Color: 49D/138D.

*Peduncle.*—Aspect: Strong, erect, rigid, and upright. Length: 3 to 5 mm. Texture: Glabrous. Color: 138B.

*Reproductive organs.*—Stamens: Stamen number 8. Anther size: 0.3 mm. Anther shape: Flat, elliptic. Anther color: Approximately 150D. Pollen color: Approximately 12A. Pistils: Pistil number: 4. Stigma shape: Flat. Stigma appearance: Crystalline. Stigma color: 8D. Style length: 8 mm. Style color: 138D. Ovary number: 4-celled. Ovary color: Green.

Disease Resistance: No known Kalanchoe diseases observed to date.

Seed Production: Seed production has not been observed.

CHART A

| CHARACTERISTIC | KERINCI | KIEBESSY |
|---|---|---|
| PLANT HEIGHT | 22 cm | 25 cm |
| GROWTH RATE | Rapid | Moderate |
| CROP TIME | 10.5 to 15 weeks | 11 to 16 weeks |
| TIME TO FLOWER | 7.5 to 11 weeks | 8 to 11.5 weeks |
| NUMBER OF LATERAL BRANCHES | 6 to 7 | 5 to 6 |
| LATERAL BRANCH LENGTH | 19 cm | 22 cm |
| QUANTITY OF LEAVES PER LATERAL BRANCH | 10 to 15 | 8 to 13 |
| YOUNG LEAF COLOR, UPPER SIDE | 137A | 137A/147A |
| YOUNG LEAF COLOR, UNDER SIDE | 137B | 137C/147B |
| MATURE LEAF COLOR, UPPER SIDE | 137A | 147A |
| MATURE LEAF COLOR, UNDER SIDE | 137B | 147B |
| LEAF LENGTH | 11.5 cm | 12.5 cm |
| LEAF WIDTH | 8 cm | 9.5 cm |
| FLOWER DIAMETER | 1.7 cm | 1.8 cm |
| FLOWER LONGEVITY | 17 days | 19 days |
| PETAL COLOR WHEN OPENING | 52A | 52A |
| MATURE PETAL COLOR, UPPER SIDE | 52B | 58C |
| MATURE PETAL COLOR, UNDER SIDE | 49D/50D | 55B/55C/55D |
| PETAL COLOR, FADING TO | 55A | 55B |

It is claimed:

1. A new and distinct cultivar of Kalanchoe plant named Kerinci, as illustrated and described.

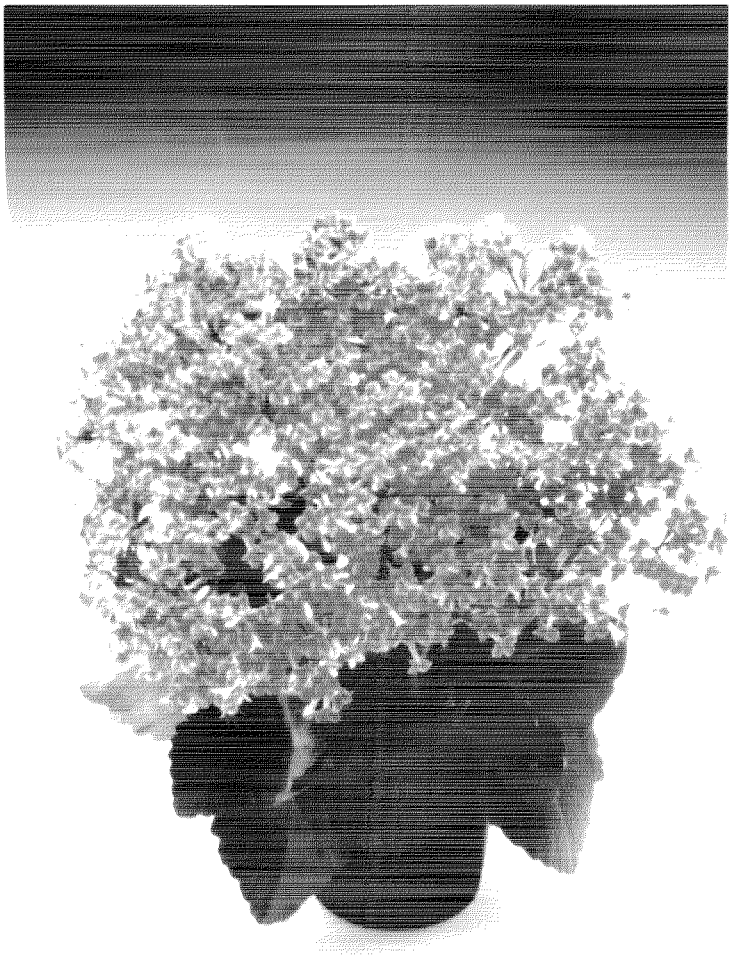

* * * * *